United States Patent
Villareal, Jr.

(10) Patent No.: US 6,354,294 B1
(45) Date of Patent: Mar. 12, 2002

(54) OXYGEN DELIVERY SYSTEM FOR PORTABLE VENTILATION

(75) Inventor: Daniel C. Villareal, Jr., West Fullerton, CA (US)

(73) Assignee: Children's Hospital of Orange County, Orange, CA (US)

(*) Notice: Subject to any disclaimer, the term of this patent is extended or adjusted under 35 U.S.C. 154(b) by 0 days.

(21) Appl. No.: 09/405,316

(22) Filed: Sep. 23, 1999

(51) Int. Cl.$^7$ .............................................. A61M 16/00
(52) U.S. Cl. ............................... 128/204.18; 128/205.24
(58) Field of Search ....................... 128/201.27, 201.28, 128/202.14, 202.22, 204.21, 204.26, 205.22–205.24, 204.18, 204.24; 137/255, 256, 907, 908

(56) References Cited

U.S. PATENT DOCUMENTS

| | | | | |
|---|---|---|---|---|
| 914,576 A | * | 3/1909 | Jaubert | 128/204.18 |
| 2,063,043 A | * | 12/1936 | McKesson | 128/29 |
| 2,216,183 A | * | 10/1940 | Connell | 128/202 |
| 2,310,021 A | * | 2/1943 | Heidbrink | 128/188 |
| 2,854,001 A | * | 9/1958 | Humblet | 128/205.22 |
| 3,016,053 A | * | 6/1962 | Medovick | 128/142 |
| 3,524,444 A | * | 8/1970 | Ellard et al. | 128/201.27 |
| 3,595,229 A | * | 7/1971 | Duck et al. | 128/205.22 |
| 3,675,649 A | * | 7/1972 | Basham et al. | 128/205.22 |
| 3,791,403 A | * | 2/1974 | Folkerth | 137/343 |
| 4,722,333 A | * | 2/1988 | Bartos | 128/205.22 |
| 4,928,682 A | * | 5/1990 | Stevenson et al. | 128/202.26 |
| 4,932,401 A | * | 6/1990 | Perkins | 128/203.12 |
| 4,944,292 A | * | 7/1990 | Gaeke et al. | 128/204.18 |
| 5,396,885 A | * | 3/1995 | Nelson | 128/204.18 |
| 5,584,289 A | * | 12/1996 | Wise | 128/205.24 |
| 5,613,490 A | * | 3/1997 | Mayes et al. | 128/205.22 |
| 5,647,346 A | * | 7/1997 | Holscher | 128/202.22 |
| 5,676,135 A | * | 10/1997 | McClean | 128/205.22 |
| 5,785,050 A | * | 7/1998 | Davidson et al. | 128/205.24 |
| 6,082,359 A | * | 7/2000 | Preston | 128/205.24 |

* cited by examiner

*Primary Examiner*—John G. Weiss
*Assistant Examiner*—Teena Mitchell
(74) *Attorney, Agent, or Firm*—Knobbe, Martens, Olson & Bear, LLP

(57) ABSTRACT

A portable oxygen delivery system supplies oxygen during prolonged transport via ambulance or helicopter to patients who are critically ill and in need of ventilatory support. The system includes two sets of oxygen tanks delivering oxygen to a manifold having two valve regulators. Oxygen flows from the first set of oxygen tanks through the first valve regulator, which remains open while the second valve regulator is closed, to the patient's portable ventilator. When the pressure from the first set of tanks drops below a given threshold, the first valve regulator closes and the second valve regulator opens, allowing oxygen to flow from the second set of oxygen tanks through the second valve regulator to the patient's ventilator. This system thereby maintains a continuous flow of oxygen to the patient's ventilator.

10 Claims, 2 Drawing Sheets

OXYGEN DELIVERY SYSTEM FOR PORTABLE VENTILATION

BACKGROUND OF THE INVENTION

1. Field of the Invention

The present invention relates to portable ventilator systems used in transporting critically ill patients, and more particularly, to a system of dual sets of oxygen tanks delivering oxygen to a high-flow switchover manifold apparatus.

2. Description of the Related Art

Critically ill patients with respiratory failure require mechanical, assisted ventilation. When they are being transported to and from the hospital, for example in an ambulance or helicopter, such patients are typically given ventilatory assistance manually by means of a bag mask (e.g., Ambu™ bag) and 100% oxygen delivered from an oxygen tank. Such a bag mask consists of a face mask that fits over the patient's nose and mouth, and an attached hand-held bag for manually inflating and deflating the patient's lungs. Such bag-mask ventilation is inherently unreliable because it depends on the skill and judgment of the operator of the bag mask to inflate and deflate the patient's lungs at the proper frequency and tidal volume. As a result, wide interoperator variation is observed in a given patient's delivered tidal volume and respiratory rate. In addition, wide intraoperator variation is also observed from patient to patient by the same operator because of differences in patient size, lung compliance, and other factors.

This means that the patient may be over- or underventilated, depending on the minute ventilation, which is the product of respiratory rate and tidal lung volume, being delivered by the operator. As a result, significant hypercapnia from $CO_2$ retention by the patient, with concomitant respiratory acidosis; or hypocapnia, with concomitant respiratory alkalosis, may occur. When respiratory acidosis occurs as the result of underventilation, it compounds any underlying metabolic acidosis, such as lactic acidosis caused by poor tissue oxygenation (which is nearly always present in patients with respiratory failure), or diabetic ketoacidosis caused by inadequate insulin availability. In transport situations, this problem is worsened, as the acid-base balance and oxygenation status of the patient are unknown because one cannot readily perform an arterial blood gas analysis in the field.

In addition to the inherent unreliability of operating a bag mask, there is a significant risk to the patient of barotrauma, including pneumothorax, pneumomediastinum, and subcutaneous emphysema. These complications occur primarily when relatively noncompliant lungs are overinflated, with resulting small perforations in the pleura, alveoli, or other pulmonary structures.

One problem with using mechanical ventilators in transport settings, for example in an ambulance, is that such ventilators typically require oxygen flow pressures around 40 lbs. per square inch ("psi"), which is the typical oxygen pressure in oxygen delivery systems within the walls of hospitals. Normally, ventilators are in fact connected to wall-oxygen systems in hospitals and nursing homes. Even portable ventilators, such as the VDR-3C Universal Logistical Precussionator Ventilator, available from Percussionaire Corporation, is designed for use with low-pressure (e.g., 40 psi) oxygen delivery systems. Oxygen tanks, on the other hand, although portable, deliver oxygen at pressures typically from 100 to 2,200 psi, which is too high for delivery to mechanical ventilators.

In addition, there is a problem in delivering adequate quantities of oxygen for prolonged transport using a mechanical ventilator. Typically, one or two oxygen tanks will not last a sufficiently long period to allow patients to be mechanically ventilated with a moderate to high fraction of inspired oxygen ("$FIO_2$") (e.g., 100% $FIO_2$) over the course of a trip of, for example, 20–40 minutes duration.

SUMMARY OF THE INVENTION

The present invention addresses the need for an oxygen delivery system that can enable high-flow, high-pressure oxygen tanks to be adapted to portable mechanical ventilators, and that will allow sufficient oxygen to be administered throughout the course of prolonged transport of a patient while retaining portability.

There is provided in accordance with one aspect of the present invention an oxygen delivery system for portable mechanical ventilation. The oxygen delivery system includes at least a first set and a second set of individual oxygen tanks. A first intake tube is interposed between the first set of oxygen tanks and a first regulator, and the first regulator contains a valve which remains open until the pressure of oxygen flowing through the first regulator drops below a predetermined threshold pressure level. A second intake tube is interposed between the second set of oxygen tanks and a second regulator, and the second regulator contains a valve which remains closed until the pressure in the second regulator drops to approximately the predetermined threshold pressure level. One or more outtake tubes connect the first and second regulators, and a central tube is interposed between these outtake tubes and a mechanical ventilator.

In accordance with one aspect of the present invention, the threshold pressure level is within the range of 90 to 100 pounds per square inch. In a firther aspect of the present invention, there are only two sets of oxygen tanks.

In a further aspect of the present invention, one or more pressure gauges are attached to the regulators. In other aspects of the present invention, one or more pressure gauges are attached to the central tube and measure the pressure of oxygen flowing to the mechanical ventilator.

In accordance with another aspect of the present invention, there is provided a method of delivering oxygen to a portable ventilator during transport of a patient. The method includes providing a first set of oxygen tanks connected by tubing to a first regulator, and providing a second set of oxygen tanks connected by tubing to a second regulator. The method further includes causing a valve within the first regulator to close when the oxygen pressure within the first regulator drops below a particular pressure threshold, thereby causing the flow of oxygen through the first regulator to cease; and causing a valve within the second regulator to open at approximately the same threshold pressure, thereby causing oxygen to flow from the second set of oxygen tanks through the second regulator to the patient's ventilator.

DESCRIPTION OF THE PREFERRED EMBODIMENT

Figure 1:
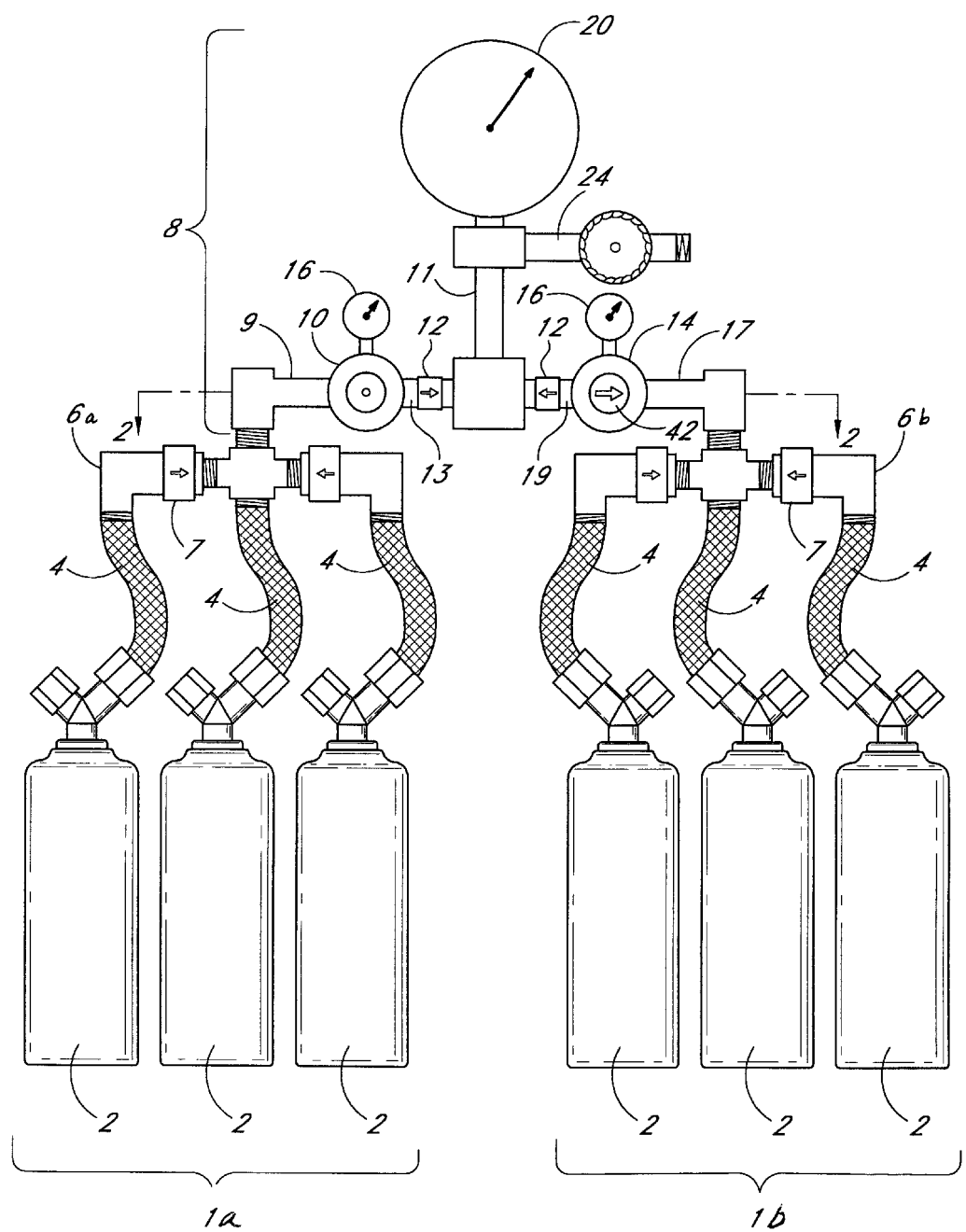
FIG. 1 is a schematic front view of the high-flow switchover manifold apparatus used in conjunction with two sets of oxygen tanks.

FIG. 1 illustrates an oxygen delivery system and high-flow switchover manifold apparatus for use in mechanical ventilation during transport. Although the description below is primarily directed to transporting pediatric and neonatal patients, the system and apparatus described may be used eoually well in transporting adults.

In the illustrated embodiment, the oxygen delivery system includes two sets of oxygen tanks 1a and 1b. Both the first set of oxygen tanks 1a and the second set of oxygen tanks 1b has three individual oxygen tanks 2. In other embodiments, fewer or more than three oxygen tanks can be utilized. Each oxygen tank is connected by a hose 4 to a yoke device 6a, 6b which entrains oxygen from all three tanks 2 by one or more one-way valves 7. In other embodiments, there may be no one-way valves 7 present, and the system can be operative without these one-way valves.

The oxygen delivery system includes a high-flow switchover manifold apparatus 8. The high-flow switchover manifold apparatus includes, among other parts, a first intake tube 9, and a first regulator 10, a second intake tube 17, a second regulator 14, one or more one-way valves 12, central tubing 11, a pressure gauge 20, and an export tube 24. The first regulator 10 contains a one-way valve (shown as 32 in FIG. 2). Similar to the first regulator 10, the second regulator 14 has a valve within it (shown as 32 in FIG. 2). In one embodiment, the oxygen flow pressure through each regulator 10, 32 can be read on one or more external gauges 16. Alternatively, no external gauges need be present. A first outtake tube 13 and a second outtake tube 19 are connected to the first regulator 10 and the second regulator 14, respectively. The outtake tubes 13, 19 can each may have one or more one-way valves 12, and a central tube 11 within the manifold apparatus 8. An export tube 24 attached to the central tube 11 leads to the patient's ventilator (not pictured). One or more additional pressure gauges 20 connected to the manifold allow measurement of the pressure of or flow rate of oxygen flowing through the export tube 24 to the patient's ventilator.

In some embodiments, there are one or more one-way valves 12 positioned within the tubing. In other embodiments, no one-way valves 12 are present. A flow indicator knob 42 can also be present in certain embodiments to indicate to the operator which sets of oxygen tanks is being utilized.

Entrained oxygen flows into the high-flow switchover manifold apparatus 8. The oxygen flowing through the yoke device 6a, 6b attached to the first set of oxygen tanks 1a flows into the first intake tube 9 of the manifold apparatus 8. Oxygen then flows into the first regulator 10. The one-way valve (shown as 32 in FIG. 2) of the first regulator 10 is opened while oxygen flows at high pressure or flow rates from the first set of oxygen tanks 1. As used herein, the term "regulator" is any device with an input port and an output port for flowing fluid (in either the gas or liquid state) into and out of the device, respectively, and that serves to control the output pressure of fluid. In one embodiment, the oxygen flow pressure in the first regulator 10 or the second regulator 14 may be read on one or more external gauges 16. In other embodiments, however, it is not necessary to include any external gauges. From the regulator 10, oxygen flows through a first outtake tube 13. The outtake tube 13 can have one or more one-way valves 12 within it to maintain the flow of oxygen in one direction. In other embodiments, no one-way valves 12 are present in the outtake tube 13. Oxygen next flows from the outtake tube 13 and the central tube 11 to the export tube 24. From the export tube 24, oxygen flows into the patient's ventilator (not pictured). One or more additional pressure gauges 20 can be attached to the export tube 24, to measure the pressure or flow rate of oxygen flowing through the export tube 24 to the patient's ventilator.

As oxygen flows from the first set of oxygen tanks 1a through the first regulator 10, the second regulator 14 is closed to oxygen flow. More specifically, the second regulator 14 has a valve within it (shown in FIG. 2) which remains closed approximately as long as oxygen is flowing through the valve within the first regulator 10.

Oxygen flowing through the first regulator is generally at a pressure of 70 to 2,200 psi. When the oxygen pressure drops below a particular threshold, typically between 90 and 100 psi, the valve 32 within the first regulator 10 closes and, at approximately the same time or at approximately the same threshold pressure, the valve 32 within the second regulator 14 opens, thereby allowing oxygen to flow from the second set of oxygen tanks 1b through a set of tubes 4 and through a second yoke device 6b. This phenomenon is referred to herein as a "switchover" of oxygen flow. The predetermined pressure level, which triggers valve closing or valve opening, can be a discrete pressure level, or it can be within a range of pressures. As used herein, "approximately" the same threshold pressure means within about 50 psi of the same threshold pressure, and preferably within about 10 psi.

After the switchover, oxygen flows into a second intake tube 17, through the second regulator 14 into the second output tube 19. In some embodiments, there are one or more one-way valves 12 positioned within the tubing. In other embodiments, no one-way valves 12 are present. Oxygen thence flows from a second output tube 19 into the central tube 11 and through the export tube 24 into the patient's ventilator. The switchover occurs as the first regulator 10 closes while the second regulator 14 opens. In a preferred embodiment, the switchover of oxygen flow from the first set of oxygen tanks 1a to the second set of oxygen tanks 1b occurs approximately at the same time, typically between 70 and 120 psi and preferably around 90 to 100 psi. In other embodiments, the second valve 14 opens prior to the closing of the first valve such that oxygen is flowing from both sets of oxygen tanks 1a and 1b simultaneously. A flow indicator knob 42 can also be present in certain embodiments. This allows the operator to turn the flow indicator knob 42 to indicate which set of oxygen tanks is currently flowing oxygen to the patient's ventilator.

One type of the first regulator 10 and second regulator 14 is herein described. There are many types of regulators which will allow valves to open and/or close at predetermined pressure thresholds. These particular regulators will be apparent to those of ordinary skill in the art. One such regulator is manufactured by AirGas Corporation (Los Angeles, Calif.) and includes a central control unit high-flow switchover assembly (Part No. NEOCCU98081126), a left pigtail assembly for three cylinders (Part No. NEOLPT36061138), and a right pigtail assembly for three cylinders (Part No. NEORTP98081138).

Figure 2:
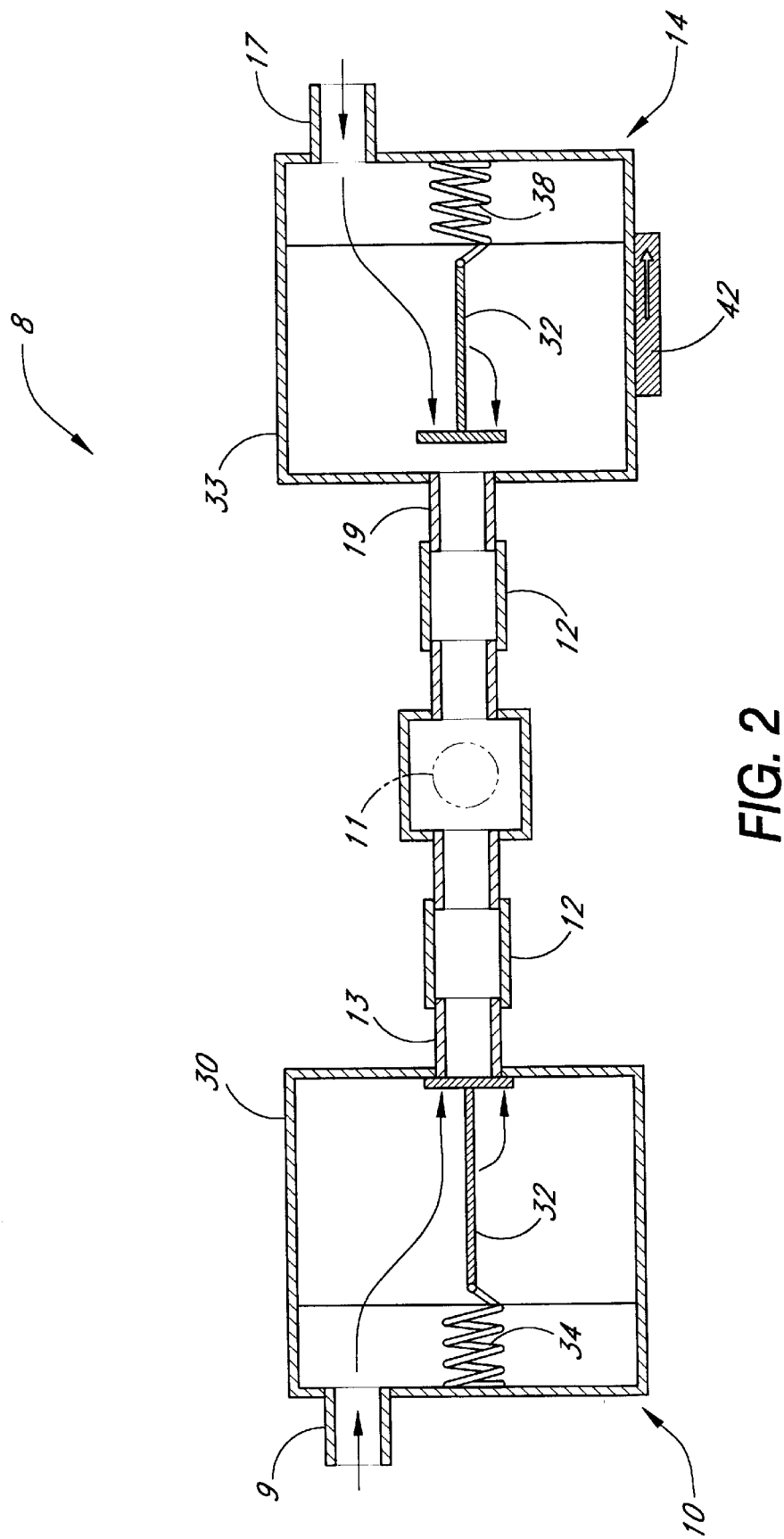
FIG. 2 is a detailed cross-sectional view of the high-flow switchover manifold apparatus taken along line 2—2 of FIG. 1.

One type of the first regulator 10 is schematically demonstrated in FIG. 2. In one embodiment of the present invention, the first regulator 10 includes a housing 30, which contains a valve 32 and a spring mechanism 34. This is shown as a simple mechanism in FIG. 2, although there is a wide variety of valve mechanisms which may accomplish the same goal, namely to have the valve 32 close when the pressure flowing from the first set of oxygen tanks 1 through the intake valve 9 drops below a certain threshold.

One type of the second regulator 14 is also illustrated in FIG. 2. The second regulator 14 includes a housing 33, which contains a valve 32, coupled to a spring mechanism 38. There is a wide variety of valve mechanisms which may accomplish the desired goal in the second regulator 14, namely to open the valve 32 when the pressure in the central tubing 11 and/or in the second outflow tube 19 drops below a predetermined threshold pressure or pressure range. These mechanisms will be readily apparent to those of skill in the art. For example, the valve mechanisms within the regulators (10 and 14) can be controlled electronically. Alternatively, the regulators can be mechanically controlled by simple hydraulics, pneumatics, or fluid mechanics, relying on, for example, absolute pressure or flow through the regulators or the intake tubes (9 and 17), outtake tubes (13 and 19), central tube 11, or comparative pressures or flows between the two regulators (10 and 14) and/or tubes. For example, an electronic or mechanical sensor can sense the time, or approximate time, when oxygen flow through the first regulator has ceased, and an electronic or mechanical signal can be sent to trigger the opening of the valve in the second regulator.

The embodiment illustrated in FIG. 2 shows a spring mechanism 38 which is designed to keep the valve 32 closed until the pressure in the central tubing 11 as well as the second outflow tube 19 drops below a certain threshold, for example 90 to 100 psi. Once this pressure drops below the preset threshold, the valve 32 within the second regulator 14 opens, allowing oxygen to flow through the second intake tube 17 into the regulator 14 and thence into the second outflow tube 19 the central tube 11, and onto the patient's ventilator through the export tube 24. Also illustrated is the flow indicator knob 42, which can be present in certain embodiments. The operator can turn the flow indicator knob 42 to indicate which set of oxygen tanks is currently flowing oxygen to the patient's ventilator.

In a further embodiment of the present invention, the second regulator 14 may have a valve which remains closed until oxygen flow through the first regulator 10 ceases. The information concerning the oxygen flow through the first regulator 10 may be sensed electronically or mechanically, in ways that are well known to those of skill in the art, and that information may be transmitted to the second regulator 14 in order to trigger the valve opening in the second regulator 14.

As used herein and as pertaining to valves, "open" means substantially open, permitting oxygen to flow through a valve. Furthermore, as used herein and as pertaining to valves, "closed" means substantially closed, limiting the flow of oxygen through a valve relative to the "open" position of the valve. Also, when it is stated that one causes the flow of oxygen through the first regulator to "cease," it is meant that the flow of oxygen through the first regulator diminishes greatly, if not totally ceases.

Other embodiments in the invention will become apparent to those of skill in the art in view of the disclosure herein. Accordingly the scope of the present invention is not intended to be limited by the foregoing, but rather by reference to the attached claims.

What is claimed is:

1. An oxygen delivery system for portable mechanical ventilation, comprising:

a first set of oxygen tanks;

a second set of oxygen tanks;

a first regulator removably coupled to the first set of oxygen tanks;

a valve within the first regulator, the valve being open while oxygen flowing through the first regulator is at greater than a predetermined pressure level, and the valve being closed while oxygen flowing through the first regulator is at less than the predetermined pressure level;

a second regulator removably coupled to the second set of oxygen tanks; and a valve within the second regulator, the valve being closed while oxygen flowing through the first regulator is at greater than the predetermined pressure level, and the valve being open while oxygen flowing through the first regulator is at less than the predetermined pressure level;

wherein the first and second regulators are in communication with a mechanical ventilator.

2. The system of claim 1, additionally comprising a third set of oxygen tanks, and a third regulator removably coupled to the third set of oxygen tanks.

3. The system of claim 1, wherein the predetermined pressure level is within the range of 70 to 120 pounds per square inch.

4. The system of claim 3, wherein the predetermined pressure level is within the range of 90 to 100 pounds per square inch.

5. The system of claim 1, wherein one or more pressure gauges are in communication with the first and second regulators.

6. The system of claim 5, wherein each set of oxygen tanks includes three individual oxygen tanks.

7. The system of claim 1, wherein each set of oxygen tanks includes one or more individual oxygen tanks.

8. An oxygen delivery system for portable mechanical ventilation, comprising:

a first set of oxygen tanks;

a second set of oxygen tanks;

a first regulator removably coupled to the first set of oxygen tanks;

a valve within the first regulator, the valve being open while oxygen flowing through the first regulator is at greater than a predetermined pressure level, and closed while oxygen flowing through the first regulator is at less than the predetermined pressure level;

a second regulator removably coupled to the second set of oxygen tanks; and a valve within the second regulator, the valve being closed while oxygen flows through the first regulator, and opening approximately when oxygen flow through the first regulator ceases;

wherein the first and second regulators are in communication with a mechanical ventilator.

9. The system of claim 8, wherein the valve in the second regulator opens prior to the closing of the valve within the first regulator.

10. A method of delivering oxygen to a portable ventilator during transport of a patient, comprising:

providing a first set of oxygen tanks removably coupled to a first regulator, which is in communication with a mechanical ventilator;

providing a second set of oxygen tanks removably coupled to a second regulator, which is in communication with a mechanical ventilator;

flowing oxygen from the first set of oxygen tanks through the first regulator to the ventilator;

closing a valve within the first regulator when an oxygen pressure within the first regulator is less than a predetermined pressure, thereby causing the flow of oxygen through the first regulator to cease; and opening a valve within the second regulator at approximately the predetermined pressure, thereby causing oxygen to flow from the second set of oxygen tanks through the second regulator to the ventilator.

* * * * *